(12) United States Patent
King et al.

(10) Patent No.: US 9,606,054 B2
(45) Date of Patent: Mar. 28, 2017

(54) METHODS, SAMPLING DEVICE AND APPARATUS FOR TERAHERTZ IMAGING AND SPECTROSCOPY OF COATED BEADS, PARTICLES AND/OR MICROPARTICLES

(71) Applicant: Advantest Corporation, Tokyo (JP)

(72) Inventors: Edward E. King, Dayton, OH (US); David A. Heaps, Yardley, PA (US); Gregory Scott Self, El Dorado Hills, CA (US); Richard R. McKay, East Windsor, NJ (US); Mark J. Sullivan, Framingham, MA (US)

(73) Assignee: ADVANTEST CORPORATION, Tokyo (JP)

( * ) Notice: Subject to any disclaimer, the term of this patent is extended or adjusted under 35 U.S.C. 154(b) by 33 days.

(21) Appl. No.: 14/042,431

(22) Filed: Sep. 30, 2013

(65) Prior Publication Data
US 2015/0090881 A1    Apr. 2, 2015

(51) Int. Cl.
*G01N 21/3586*    (2014.01)
(52) U.S. Cl.
CPC ................. *G01N 21/3586* (2013.01)
(58) Field of Classification Search
CPC ........... G01N 21/3586; G01N 21/3581; G01N 2021/258
USPC .... 250/338.1, 341.8, 339.06, 339.08, 339.11
See application file for complete search history.

(56) References Cited

U.S. PATENT DOCUMENTS 3,800,940 A  *  4/1974  Thomas ........................ 206/533
5,973,316 A     10/1999  Ebbesen et al.
6,052,238 A     4/2000   Ebbesen et al.
6,078,047 A     6/2000   Mittleman et al.
6,443,307 B1 *  9/2002   Burridge ....................... 206/532
7,498,577 B2    3/2009   Kurosaka et al.
7,551,269 B2    6/2009   Itsuji
7,649,633 B2    1/2010   Kawate
7,683,325 B2    3/2010   Sekiguchi et al.
(Continued)

FOREIGN PATENT DOCUMENTS

EP    2031374 A2    3/2009
JP    11-072607     3/1999
(Continued)

OTHER PUBLICATIONS

May, R. K., et al., "Terahertz in-line sensor for direct coating thickness measurement of individual tablets during film coating in real-time", 2011, J. Pharm. Sci., 100: 1535-1544.*
(Continued)

*Primary Examiner* — David Porta
*Assistant Examiner* — Blake Riddick

(57) ABSTRACT

A holder and apparatus for terahertz imaging and/or spectroscopy of beads, particles or microparticles, and methods for terahertz imaging and/or spectroscopy of beads, particles or microparticles and making the holder are disclosed. The holder includes a tray having a substantially planar upper surface, and one or more offsets above or below the substantially planar upper surface. Each offset is configured to hold one of the beads, particles or microparticles, and has a height or depth configured to minimize or eliminate interference between reflections of the terahertz radiation from the tray and reflections of the terahertz radiation from the bead, particle or microparticle in or on the offset.

24 Claims, 12 Drawing Sheets

(56) References Cited

U.S. PATENT DOCUMENTS

| | | | |
|---|---|---|---|
| 7,781,736 | B2 | 8/2010 | Logan, Jr. et al. |
| 7,795,582 | B2 | 9/2010 | Jez et al. |
| 8,271,128 | B1* | 9/2012 | Schultz .................. 700/236 |
| 8,712,163 | B1* | 4/2014 | Osheroff .................. 382/195 |
| 2003/0021734 | A1* | 1/2003 | Vann et al. .................. 422/100 |
| 2003/0063123 | A1* | 4/2003 | Fukube et al. .................. 345/771 |
| 2003/0063487 | A1* | 4/2003 | Steckl et al. .................. 365/106 |
| 2003/0152194 | A1* | 8/2003 | Nordmeyer et al. .......... 378/73 |
| 2003/0198619 | A1* | 10/2003 | Dong et al. .................. 424/85.7 |
| 2004/0061055 | A1 | 4/2004 | Kawase et al. |
| 2004/0241748 | A1* | 12/2004 | Ault-Riche et al. .......... 435/7.1 |
| 2005/0075335 | A1 | 4/2005 | Buxton et al. |
| 2005/0098728 | A1* | 5/2005 | Alfano et al. .............. 250/341.8 |
| 2005/0173637 | A1* | 8/2005 | Abrahamson ........ G01N 21/359 250/341.1 |
| 2005/0216075 | A1* | 9/2005 | Wang et al. .................. 623/1.15 |
| 2005/0253071 | A1 | 11/2005 | Ferguson et al. |
| 2006/0000470 | A1* | 1/2006 | Clarke et al. ............. 128/200.23 |
| 2006/0029941 | A1* | 2/2006 | Koo et al. .......................... 435/6 |
| 2006/0043298 | A1 | 3/2006 | Kawase et al. |
| 2006/0045807 | A1 | 3/2006 | Zhang et al. |
| 2006/0054824 | A1 | 3/2006 | Federici et al. |
| 2006/0228897 | A1* | 10/2006 | Timans .......................... 438/758 |
| 2006/0237650 | A1 | 10/2006 | Taday |
| 2007/0138392 | A1 | 6/2007 | Cole |
| 2007/0222693 | A1* | 9/2007 | Popa-Simil .................. 343/753 |
| 2007/0229094 | A1 | 10/2007 | Kasai et al. |
| 2007/0257216 | A1* | 11/2007 | Withers ............. G01N 21/3581 250/580 |
| 2008/0239317 | A1* | 10/2008 | Schulkin et al. ............. 356/365 |
| 2009/0128799 | A1 | 5/2009 | MacHattie et al. |
| 2010/0024999 | A1 | 2/2010 | Haran et al. |
| 2010/0066639 | A1* | 3/2010 | Ngyuen et al. ........... 343/911 R |
| 2010/0102256 | A1* | 4/2010 | Andrew et al. ............ 250/505.1 |
| 2010/0108889 | A1* | 5/2010 | Shen et al. .................. 250/341.1 |
| 2010/0148070 | A1 | 6/2010 | Ho et al. |
| 2012/0037804 | A1 | 2/2012 | Federici |
| 2012/0225475 | A1* | 9/2012 | Wagner et al. ............ 435/288.7 |
| 2012/0304756 | A1 | 12/2012 | White et al. |
| 2013/0075699 | A1* | 3/2013 | Brown et al. .................... 257/21 |
| 2013/0153767 | A1* | 6/2013 | Savoy et al. ............... 250/338.1 |
| 2013/0204577 | A1 | 8/2013 | Savard et al. |
| 2013/0221082 | A1* | 8/2013 | Botten .................... G06F 17/30 235/375 |
| 2013/0270596 | A1* | 10/2013 | Senellart et al. ............... 257/98 |
| 2014/0252231 | A1* | 9/2014 | Tomioka ............ G01N 21/3581 250/338.1 |

FOREIGN PATENT DOCUMENTS

| | | |
|---|---|---|
| JP | 2004-108905 | 4/2004 |
| JP | 2004-117703 | 4/2004 |
| JP | 2007010366 | 1/2007 |
| WO | 2009156468 A1 | 12/2009 |

OTHER PUBLICATIONS

International Search Report (ISR) for PCT/JP2008/051404 for Examiner Consideration, Citing US Patent Application Nos. 1-2 and Foreign Patent Document Nos. 1-2 Listed Above, Apr. 22, 2008.

Japanese Office Action dated Apr. 3, 2012, in a counterpart Japanese patent application No. 2007-021660. (Cited references have been submitted in a previous IDS).

Japanese Office Action dated Sep. 20, 2011, in a counterpart Japanese patent application No. 2007-021660, citing JP 2007-010366, JP H11-072607 and Lamarre et al., "Metallic Mesh Properties and Design of Submillimeter Filters", Ogawa et al., "Usugata Kinzoku Mesh no Toka Tokusei O Riyo shita Sensor Oyo", and Ogawa et al., "Printable Mesh O Mochiita Terahertz-tai Kussetsuritsu Sensor", which have been submitted in a previous IDS. A machine translation (not reviewed for accuracy) attached.

Lamarre et al., "Metallic Mesh Properties and Design of Submillimeter Filters", International Journal of Infrared and Millimeter Waves, vol. 2, 1981, pp. 273-292. Cited in ISR and mentioned on p. 2 of as-filed specification.

Acevedo, David, Evaluation of Three Approaches for Real-Time Monitoring of Roller Compaction with Near-Infrared Spectroscopy, Jul. 24, 2012, AAPS PharmSciTech, vol. 13, pp. 1005-1012.

Ogawa et al., "Printable Mesh O Mochiita Terahertz-tai Kussetsuritsu Sensor", Dai 66 Kai Extended abstracts; the Japan Society of Applied Physics, Sep. 7, 2005, Dai 66 Kai, separate vol. 3, p. 966, 9a-P6-26. Cited in ISR as concise explanation of relevance.

Ogawa et al., "Usugata Kinzoku Mesh no Toka Tokusei O Riyo shita Sensor Oyo", Dai 67 Kai Exended abstracts; The Japan Society of Applied Physics, Aug. 29, 2006, Dai 67 Kai, separate vol. 3, p. 1016, 31p-za-2. Cited in ISR as concise explanation of relevance.

Sakai, "Terahertz Time-Domain Spectroscopy" Spectroscopy Studies, vol. 50, No. 6, pp. 261-273, 2001, Kobe, Japan. Mentioned on p. 1 of As-Filed Specification As Concise Explanation of Relevance.

Written Option (PCT/ISA/237) of PCT/JP2008/051404, Apr. 22, 2008.

Yoshida et al., "Kinzoku Mesh ni yoru Tanpakushitsu no Label Free Kenshutsu", IEICE Technical Report, Nov. 20, 2007, vol. 107, No. 355, p. 99-102. Cited in ISR as concise explanation of relevance.

Yoshida et al., "Terahertz sensing method for protein detection using a thin metallic mesh", Applied Physics Letters, Dec. 17, 2007, vol. 91, No. 25, p. 253901-1-253901-3. Cited in ISR.

Ende, David, Chemical Engineering in the Pharmaceutical Industry: R & D to manufacturing, Mar. 10, 2011, Wiley, pp. provided.

* cited by examiner

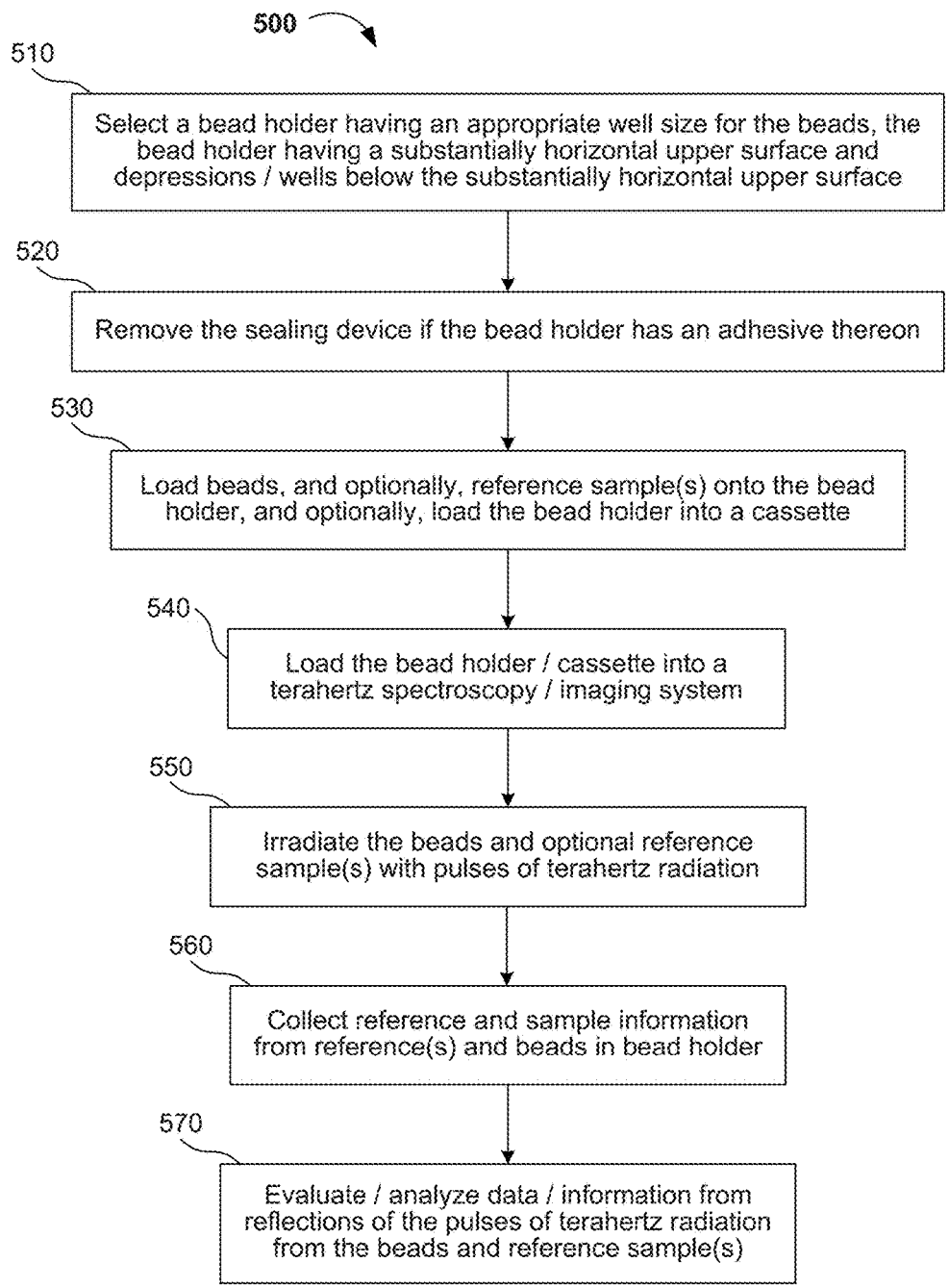

US 9,606,054 B2

METHODS, SAMPLING DEVICE AND APPARATUS FOR TERAHERTZ IMAGING AND SPECTROSCOPY OF COATED BEADS, PARTICLES AND/OR MICROPARTICLES

FIELD OF THE INVENTION

The present invention generally relates to the field of terahertz spectroscopy and/or imaging. More specifically, embodiments of the present invention pertain to methods and apparatuses for terahertz and/or time-of-flight spectroscopy and/or imaging of coated beads, particles and/or microparticles.

DISCUSSION OF THE BACKGROUND

FIG. 1 shows a conventional approach for terahertz spectroscopy and/or imaging of a bead or particle. A terahertz emitter 10 emits a pulse of radiation 20 having a frequency in the terahertz range (e.g., 0.2-100 THz), and the reflected radiation 22-26 is detected by a terahertz detector 30. In time-of-flight spectroscopy and/or imaging, a first reflection 22 from the outer surface of a coated bead 40 is detected first by the terahertz detector 30. However, part of the radiation pulse 20 passes into the outer coating 42 of the coated bead 40 on a sample mounting substrate 50 having a completely planar (e.g., horizontal) upper surface. A second reflection 24 from the outer surface of the core 44 of the coated bead 40 is detected by the terahertz detector 30 after the first reflection 22. The difference in time that the terahertz detector 30 detects the first and second reflections 22 and 24 provides information relating to the thickness of the outer coating 42. Repeating the radiation pulse emission and reflection detection at a number of different locations on the bead and/or angles between the emitter 10 and the sample mounting substrate 50 provides information relating to the uniformity of the outer coating 42.

However, reflections 26 from the completely planar upper surface of the sample mounting substrate 50 often have a time-of-flight similar to reflections 24 from the core 44 (or other layer below the surface) of the bead 40. Therefore, reflections 26 can interfere with reflections 24 from layers below the surface of the bead 40 and lead to difficulties obtaining useful or reliable information about the coating layer on a bead or particle, and sometimes can result in complete failure.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

Embodiments of the present invention relate to a holder for beads, particles or microparticles, an apparatus for terahertz spectroscopy or imaging of such beads, particles or microparticles, and methods of terahertz spectroscopic analysis or imaging of such beads, particles or microparticles and of making such a holder. The holder generally comprises a tray having a substantially planar upper surface, and one or more offsets above or below the substantially planar upper surface. Each offset is configured to hold one of the beads, particles or microparticles, and has a height or depth configured to minimize or eliminate interference between reflections of the terahertz radiation from the tray and reflections of the terahertz radiation from the bead, particle or microparticle in or on the offset.

In some embodiments of the holder, the offset(s) comprise a plurality of depressions and/or wells below the substantially planar upper surface of the tray. In other embodiments of the holder, the offset(s) comprise a plurality of projections or posts above the substantially planar upper surface of the tray. In many embodiments, the tray comprises one or more dielectric materials forming the substantially planar upper surface.

When the holder includes depressions and/or wells, the plurality of depressions and/or wells may be configured to hold beads, particles or microparticles having an average diameter or size greater than the depth of the depressions and/or wells. For example, the depressions and/or wells may have a width of from 1.5 to 5 times the depth of the depressions and/or wells. In some embodiments, each of the depressions and/or wells has a first portion at the substantially planar upper surface of the tray, and a second portion below the first portion. The second portion generally has an outer periphery entirely within an outer periphery of the first portion. Additionally or alternatively, the first portion may have an uppermost surface at a first angle or arc with respect to the substantially planar upper surface of the tray, and the second portion having an uppermost surface at a second angle or arc with respect to the uppermost surface of the first portion, the second angle or arc being equal to or greater than the first angle or arc. When the holder includes projections or posts, the plurality of projections or posts may be configured to hold beads, particles or microparticles having an average diameter or size greater than a width of the projections or posts.

In some embodiments, the holder may comprise an array of offsets having n rows and m columns, where n and m are each independently an integer of at least 2. In further embodiments, n and m are each independently an integer of at least 4, and at least one offset is reserved for holding a reference bead, particle or microparticle.

In further embodiments, the holder further comprises an adhesive on an uppermost surface of each of the offsets. In additional or alternative embodiments, the height or depth of each of the offsets (e.g., relative to the substantially planar upper surface of the tray) is from 0.1 to 3 mm.

The apparatus generally comprises terahertz spectrometers and/or imaging equipment that include the present holder and/or similar apparatuses embodying one or more of the inventive concepts disclosed herein. Thus, a further aspect of the invention relates to a terahertz spectroscopy or imaging apparatus, comprising the present holder; a terahertz radiation source, configured to irradiate beads, particles or microparticles in the holder with pulsed terahertz radiation; and a terahertz radiation detector, configured to receive the pulsed terahertz radiation reflected from the beads, particles or microparticles in the holder. The present terahertz spectroscopy or imaging apparatus may comprise a time-of-flight terahertz spectroscopy and/or imaging system.

A further aspect of the present invention relates to a method of analyzing or imaging beads, particles or microparticles, comprising loading one or more beads, particles or microparticles onto a bead holder, loading the bead holder into a terahertz spectroscopy and/or imaging system, irradiating the bead(s), particle(s) or microparticle(s) in the bead holder with pulses of terahertz radiation, and evaluating and/or analyzing data and/or information from reflections of the pulses of terahertz radiation from the bead(s), particle(s) or microparticle(s) in the bead holder. The bead holder generally comprises a tray having a substantially planar upper surface and one or more offsets above or below the substantially planar upper surface. Each offset is configured to hold one of the beads, particles or microparticles, and has a height or depth configured to minimize or eliminate interference between reflections of the terahertz radiation from the tray and reflections of the terahertz radiation from the bead, particle or microparticle in or on the offset. The method of analyzing or imaging beads, particles or microparticles is particularly applicable to coated beads, particles or microparticles.

As for the present holder, the bead holder in the method of analyzing or imaging may further comprise (i) an adhesive on an uppermost surface of each offset and/or (ii) a cover or sealing device on or over the adhesive. In such embodiments, the method may further comprise removing the cover or sealing device prior to loading the bead(s), particle(s) or microparticle(s) onto the bead holder. Each offset in the present method of analyzing or imaging is configured to hold one bead, particle or microparticle. Additionally or alternatively, the depth of each offset is less than an average diameter or size of the bead(s), particle(s) or microparticle(s) when the offset is below the substantially planar upper surface of the tray. Similarly, each offset has a width less than an average diameter or size of the bead(s), particle(s) or microparticle(s) when the offset is above the substantially planar upper surface of the tray.

The method of analyzing or imaging may further comprise loading the loaded bead holder into or onto a cassette, and loading the cassette into the imaging system. In addition, in the method of analyzing or imaging, the offset(s) may comprise an array of offsets having n rows and m columns, n and m each independently being an integer of at least 2. In such embodiments, the method may further comprise loading one or more reference beads or particles in the bead holder, and collecting reflection information from the reference bead(s) and the bead(s), particle(s) or microparticle(s) in the bead holder.

A still further aspect of the invention relates to a method of making a holder for analyzing or imaging beads, particles or microparticles, comprising forming a tray having a substantially planar upper surface, and forming one or more offsets above or below the substantially planar upper surface. Each offset is configured to hold one of the beads, particles or microparticles, and has a height above or a depth below the substantially planar upper surface configured to minimize or eliminate interference between reflections of the terahertz radiation from the tray and reflections of the terahertz radiation from the bead, particle or microparticle in or on the offset. In the method of making the holder, the tray and the offset(s) may be formed by a single injection-molding operation or by three-dimensional printing. Alternatively, the method may comprise performing a first single injection-molding operation to form the tray and the offset(s), performing a second single injection-molding operation to form a base and one or more posts or projections, each configured to support or create a unique one of the offset(s), and pressing together the tray and the offset(s) with the base and the post(s) or projection(s) to form the bead holder.

One advantage of the invention relates to the elimination of reflected radiation in the measured signal, which contaminates the data analysis. Thus, the present invention advantageously provides a holder, apparatus and method for terahertz imaging and/or spectroscopy that reduce or eliminate interference from reflections from the holder that might otherwise have a comparable time of flight to reflections from the beads, particles, microparticles or other similar samples.

These and other advantages of the present invention will become readily apparent from the detailed description of various embodiments below.

BRIEF DESCRIPTION OF THE DRAWINGS

FIG. 9 is a flow chart for an exemplary method of terahertz spectroscopy and/or imaging of a bead in accordance with the present invention.

DETAILED DESCRIPTION

Figure 1:
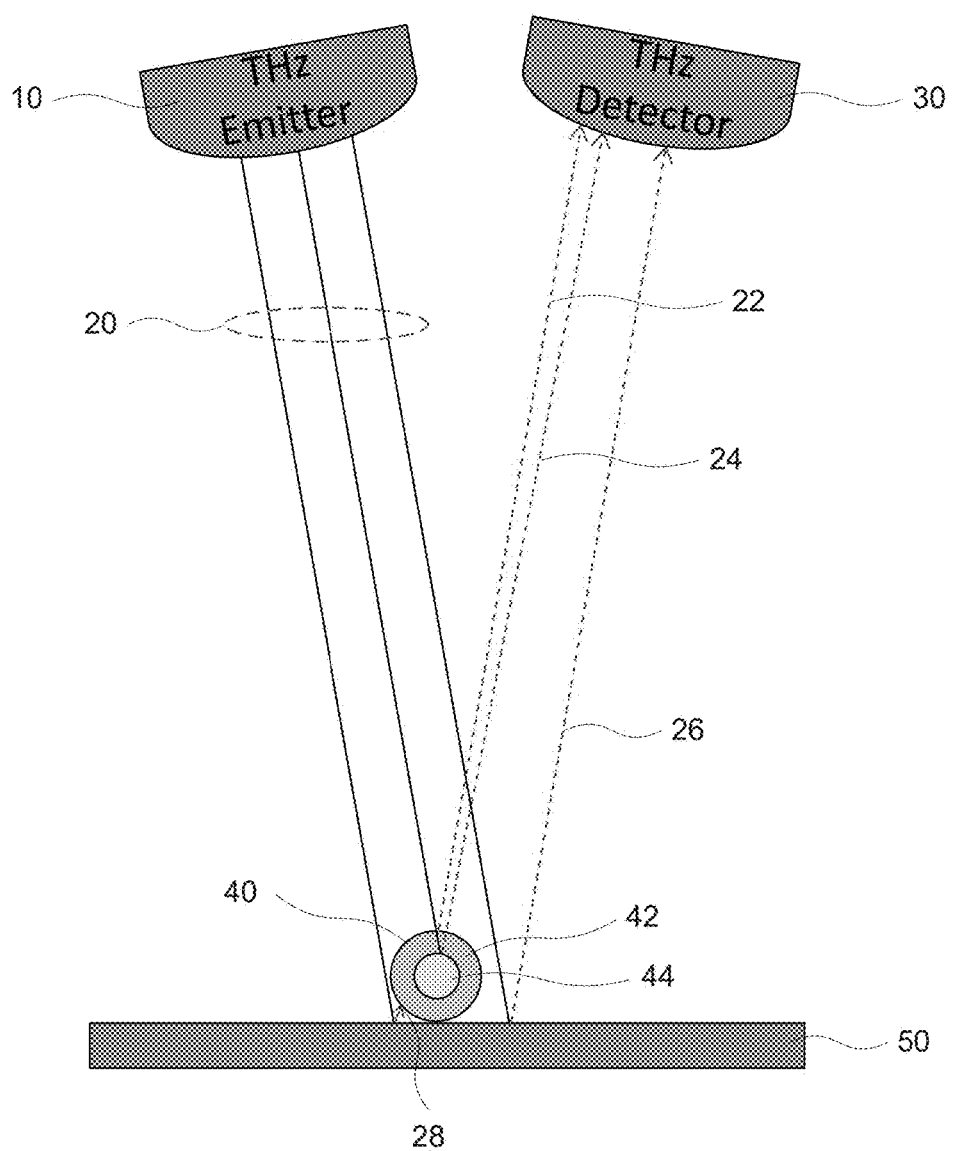
FIG. 1 is a diagram showing a conventional approach for terahertz spectroscopy and/or imaging of a bead.

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

For the sake of convenience and simplicity, the terms "bead," "particle," and "microparticle," as well as the terms "depression" and "well," are generally used interchangeably herein, and use of one of the terms in a given group (or a grammatical variation thereof) invokes the other terms (and grammatical variations thereof) unless the context of its use clearly excludes the other terms, but these terms are generally given their art-recognized meanings herein. Also, for convenience and simplicity, the terms "connected to," "coupled with," "coupled to," and "in communication with" (which terms include direct and indirect connections, couplings, and communication paths), may be used interchangeably herein, but these terms are also generally given their art-recognized meanings. Two or more nouns separated by a forward slash ("/") refer to a list of terms recited in the conjunctive or alternative; for example, "spectroscopy/imaging" refers to spectroscopy and/or imaging.

Terahertz testing (e.g., spectroscopy, imaging, or other analysis) can involve time-of-flight terahertz reflection measurements using a commercial system (e.g., a TAS7500 series terahertz spectroscopic/imaging system such as the TAS7500 IM Terahertz Imaging System commercially available from Advantest America, Inc., San Jose, Calif.). Analysis of terahertz data obtained using one or more examples of bead holders in accordance with the present invention has been validated against microscopic techniques. Measurements using the exemplary bead sample-holding device(s) of the present invention were also compared to measurements of similar samples using a non-optimized holder.

The construction of the bead holders may be by molding (e.g., injection-molding) or printing (e.g., 3-D printing). These methods provide highly accurate models which maintain highly detailed mechanical features and tolerances. The method of manufacturing the bead holder may comprise a two-part construction, a bottom part including an array of adhesive-tipped posts, and a top part including a matching array of wells or depressions into which the beads go. The top and bottom parts can be made by injection molding, are configured to mate with each other, and can be assembled merely by snapping the two parts together.

The present invention greatly reduces reflections caused by reflections of terahertz beam pulses ("beam-splash") off conventional sample holding devices. The present invention also creates a convenient way to organize and analyze multiple samples in high through-put imaging and/or spectroscopy applications.

The invention, in its various aspects, will be explained in greater detail below with regard to exemplary embodiments.

An Exemplary Holder for Coated Beads, Particles and/or Microparticles

In one aspect, the present invention relates to an apparatus for holding coated beads, particles and/or microparticles, comprising (i) a tray having a substantially planar (e.g., horizontal) upper surface, and one or more offsets above or below the substantially planar upper surface. Each offset is configured to hold one of the beads, particles or microparticles, and has a height or depth configured to minimize or eliminate interference between reflections of the terahertz radiation from the tray and reflections of the terahertz radiation from the bead, particle or microparticle in or on the offset.

Figure 2:
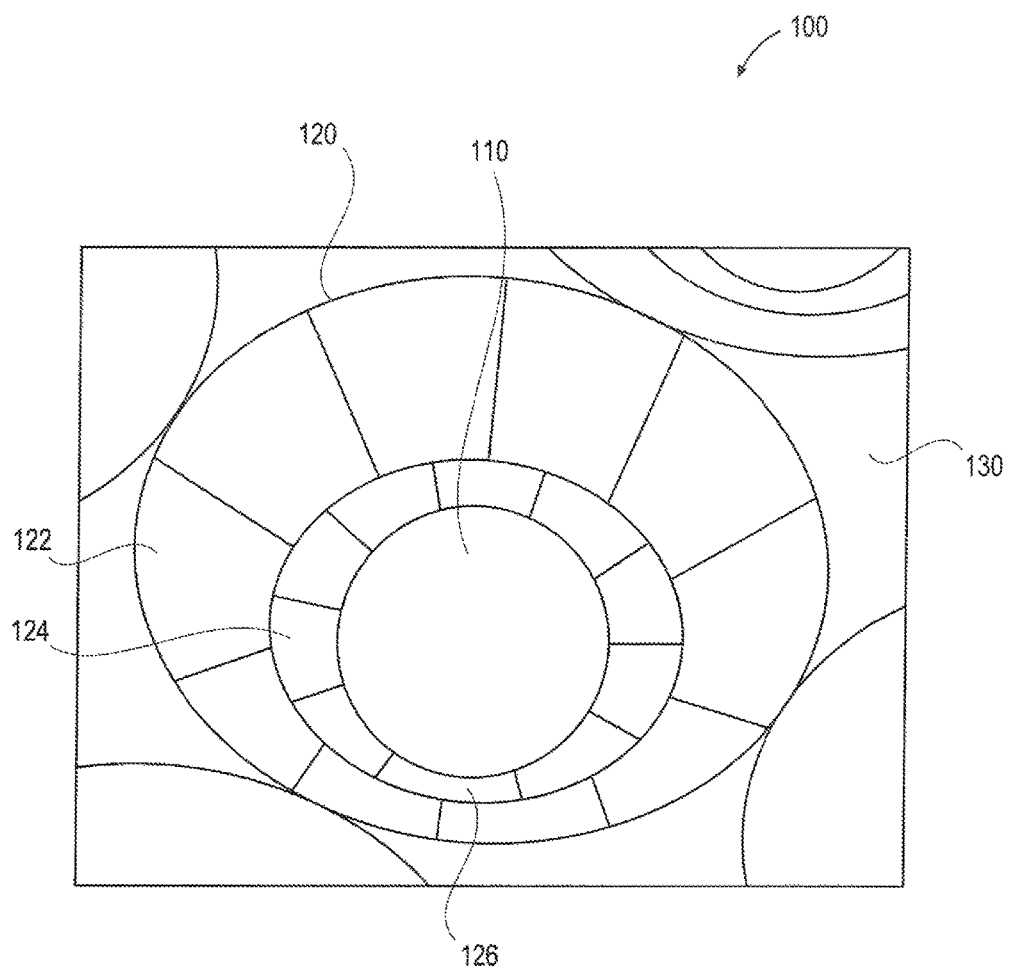
FIG. 2 is a diagram showing a sample bead in an exemplary well in an exemplary bead holder according to the present invention.

FIG. 2 shows a first exemplary bead holder 100, including a tray 130 having a substantially planar or horizontal surface and a well 120 containing a bead 110 therein. The bead 110 may be uncoated or coated with one or more coatings and/or layers, as is known in the pharmaceutical, nutrient, food supplement and/or material science fields.

The well 120 includes an upper portion 122 and a lower portion 124. The upper portion 122 is at the substantially planar/horizontal upper surface of the tray 130, and generally has a width or diameter greater than that of the bead 110. The lower portion 124 is below the upper portion 122, relative to the upper surface of the tray 130, and generally has an outer periphery entirely within the outer periphery of the upper portion 122. As shown in FIG. 2, the upper portion 122 and the lower portion 124 are concave (facing up), but the wells are not limited to this design. For example, the well 120 may have only a single portion (or shape), or may have three or more portions. For example, in some embodiments, the lower portion 124 may have an opening therein exposing an uppermost surface of a post 126 that supports the bead 110 and/or the tray 130. When the post 126 has a depression and/or well in its uppermost surface, the depression and/or well may be concave (or other shape as described herein for depressions and/or wells), thereby forming a possible third portion of the well 120 in the holder 100. Furthermore, the well 120 is not limited to a circular or spherical well. The well 120 may be oval, ellipsoid, cubic, cuboid, rectangular, parallelepiped, conical, tapered, pyramidal, elliptic paraboloid or partial elliptic paraboloid, superellipsoid, dodecahedral or semi-dodecahedral, icosahedral or semi-icosahedral, or other regular three-dimensional geometric shape.

In some embodiments, the upper portion 122 has an uppermost surface at a first angle (or, when the uppermost surface of the upper portion 122 is curved, a first arc) with respect to the substantially planar upper surface of the tray 130, and the lower portion 124 has an uppermost surface at a second angle or arc with respect to the uppermost surface of the first portion that is equal to or greater than the first angle or arc. Mathematically, when the uppermost surfaces of the upper portion 122 and the lower portion 124 are curved, a tangent of the line at the surface of the lower portion 124 just below the interface with the upper portion 122 and having the shortest distance to the upper portion 122 is equal to or greater than a tangent of the line at the surface of the upper portion 122 just below the interface with the substantially planar upper surface of the tray 130 and having the shortest distance to the substantially planar upper surface of the tray 130. When the well 120 includes an uppermost surface that is angled or curved relative to the substantially planar upper surface of the tray 130, the well 120 may further deflect or scatter portions of the terahertz radiation pulse.

The holder 100 may thus further include an opening (not shown in FIG. 2) below the lower portion 124 of the well 120, the opening having a diameter less than an average diameter or size of the beads, particles or microparticles. The center post 126 may be inserted into the opening. In such a case, the uppermost surface of the post 126 may have an adhesive thereon, to facilitate securing the bead in the well 120. Alternatively, the post 126 simply supports the tray 130 by pressing against the underside of the well 120 (and optionally fitting into a ring or opposed projections or "fins" on the underside of the well 120), and may reduce or prevent bowing or other irregularities in the substantially planar (e.g., horizontal) uppermost surface of the tray 130.

When the holder 100 is adapted for analysis of beads having relatively small dimensions (e.g., having an average size or diameter of from tenths of a millimeter to several millimeters), the depth of the well 120 in the holder 100 may be from 0.1 to 3 mm. For example, when the bead 110 has an average size or diameter of from 0.3 to 1 mm, the depth of the well 120 in the holder 100 may be from 0.1 to 0.6 mm. When the bead 110 has an average size or diameter of from 1 to 3 mm, the depth of the well 120 may be from 0.6 to 1.0 mm. When the bead 110 has an average size or diameter of from 3 to 5 mm, the depth of the plurality of depressions and/or wells may be from 1.0 to 2.0 mm. Furthermore, the well 120 may have a width of from 1.5 to 5 times the depth of the well 120 (e.g., 2-3 times, or any value or other range of values therein).

Figure 3:
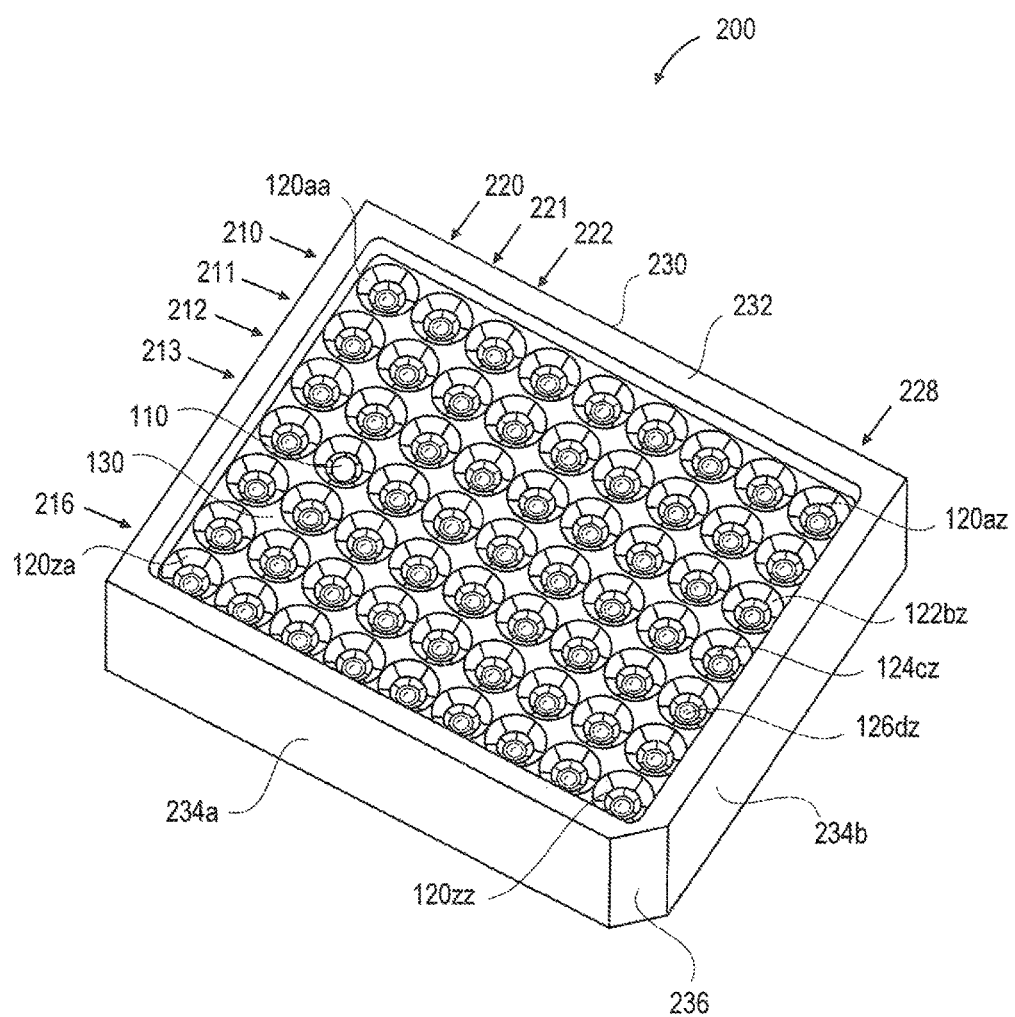
FIG. 3 is a diagram showing an exemplary multi-well bead holder according to the present invention.

FIG. 3 shows an exemplary bead holder 200, comprising a tray 130 having a substantially planar or horizontal surface, an array of wells 120aa-120zz, and a frame 230. The array of wells 120aa-120zz includes rows 210-216 and columns 220-228. While seven rows and nine columns are shown, any integer number of rows and columns (which may be independently selected or determined) of at least two is contemplated for use in the present invention. A bead 110 is shown in the well in the fourth row 213 and the second column 221. The wells 120aa-120zz generally have a configuration and/or design consistent with the discussion of well 120 in FIG. 2. Thus, FIG. 3 shows an upper portion 122bz of the well in the second row 211 and ninth column 228, a lower portion 124cz of the well in the third row 212 and ninth column 228, and a post 126dz portion 122bz exposed in the well in the fourth row 213 and ninth column 228 of the array.

The holder 200 of FIG. 3 further comprises a mechanically rigid frame 230 around a periphery of the tray 130. The frame 230 includes a support lip or protrusion 232, side walls 234a-b, and an alignment surface or notch 236. Side walls opposite to or opposing side walls 234a-b are not shown in FIG. 3, but the combination of side walls (shown and not shown) provides mechanical support for the holder 200. The support lip or protrusion 232 provides support for a cover or mask over the wells 120aa-120zz, and may provide some protection for beads in the wells 120aa-120zz. The alignment surface or notch 236 is configured to orient the holder 200 in the terahertz spectrometer and/or imaging apparatus (or in a cassette to be inserted into the terahertz spectrometer and/or imaging apparatus; discussed below with regard to FIG. 5) so that the locations of the wells in the array can be predetermined and/or known in advance.

In some embodiments, at least one well in the array is reserved for a reference bead, particle or microparticle. The well can be any location in the array, but for convenience, well 120aa in the first row 210 and first column 220 may be so reserved. In other embodiments, one row, one column, a subarray of wells in at least 2 rows and 2 columns, or another arrangement or pattern of wells (e.g., wells 120aa, 120az, 120za and 120zz at the corners of the array) may be reserved for reference beads, if desired. The reference bead may comprise or consist essentially of a bead of the same or similar size as the sample beads, coated with a relatively highly reflective material, such as a metal (e.g., gold, silver, aluminum, etc.). Ideally, the reference bead(s) comprises or consists essentially of the same bead(s) as the sample beads, having a thin layer of metal that highly reflects terahertz radiation sputtered or evaporated thereon. If a bead having a similar size is used as a reference, it can be coated (e.g., by sputtering, evaporation, etc.) independent of the sample bead. Alternatively, a reference can be made from the sample bead(s) after the sample waveform is collected by sputter or evaporation coating the sample bead(s) in the bead holder. This creates a reference of the exact geometry as the sample bead, thereby producing an exact match between the sample waveform and reference.

In many embodiments, the tray 130 comprises one or more dielectric materials that form the substantially planar upper surface. However, the tray 130 may comprise any mechanically rigid material suitable for use in terahertz spectroscopy and/or imaging. Thus, the tray 130 may comprise a sheet of a metal or alloy, such as aluminum, titanium, copper, silver, chromium, molybdenum, tungsten, nickel, gold, palladium, platinum, zinc, iron or a conventional alloy thereof, or a disc, sheet, plate or wafer of a dielectric material such as glass, plastic or other insulative polymer, or ceramic, or a laminate thereof, any of which may further include one or more additional layers and/or coatings thereon to protect or insulate the underlying material or reduce or enhance the reflective properties of the underlying material. Particular materials that are advantageous in terms of cost, processability and reflective properties include insulative thermoplastic and thermoset polymers, such as polyethylene, polypropylene, poly(tetrafluoroethylene), polyvinyl chloride, polystyrene, polyethers, polyether etherketones, polyimides, polyacrylates, polymethacrylates, polycarbonates, bisphenol polyesters, phthalate polyesters, phenol-formaldehyde copolymers, bisphenol-formaldehyde copolymers, polycarbonates, and/or and blends and copolymers thereof (e.g., acrylonitrile butadiene styrene copolymers, polycarbonate/acrylonitrile butadiene styrene blends, etc.).

Figure 4:
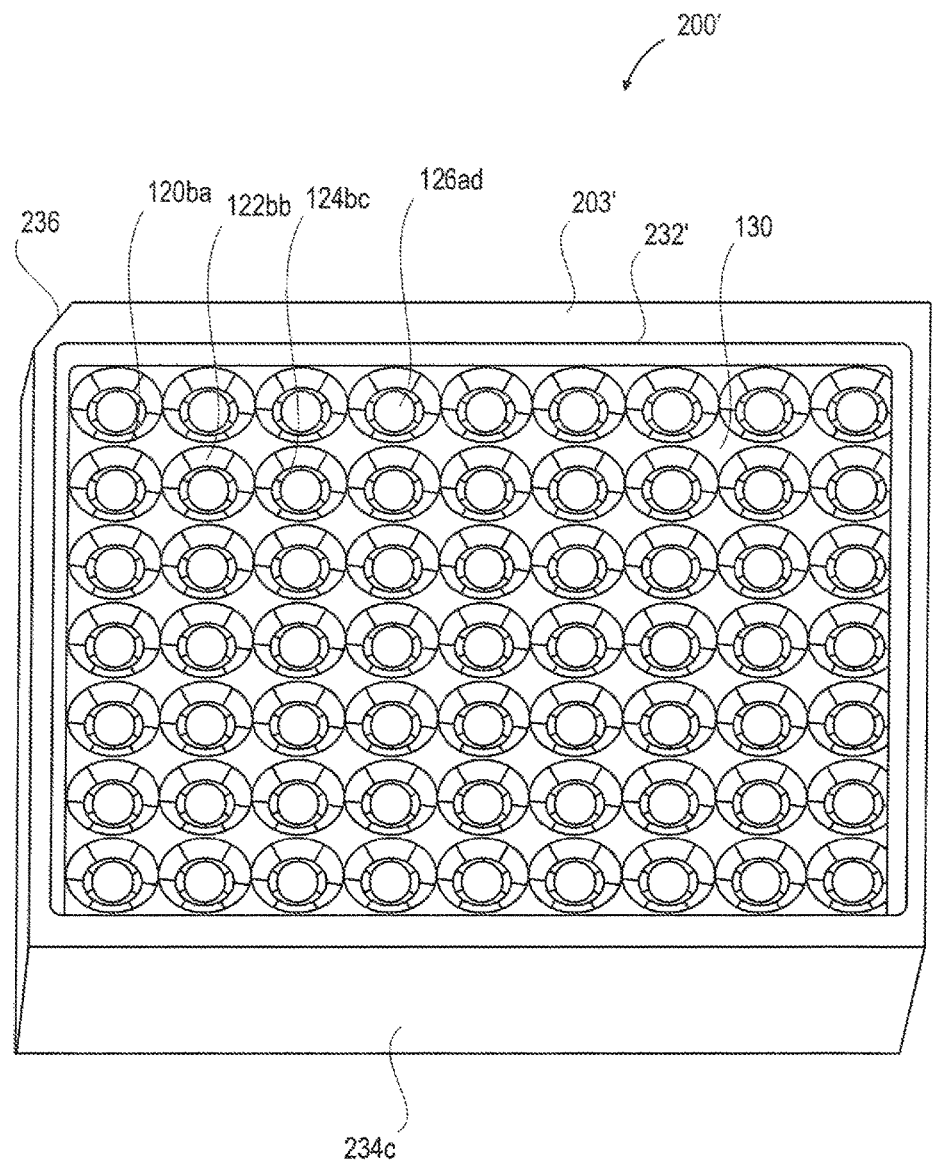
FIG. 4 is a photograph of an exemplary multi-well bead holder according to the present invention.

FIG. 4 shows a photograph of an exemplary bead holder 200' in accordance with the present invention. The bead holder 200' is a clear plastic holder designed in accordance with the holder 200 of FIG. 3, and its components are designed and/or configured similarly or identically to those of the bead holder 200 of FIG. 3. For example, the bead holder 200' comprises a tray 130 having a substantially planar and/or horizontal upper surface, an array of wells 120, and a frame 230'. The frame 230' includes a support lip 232', four side walls including sidewall 234c, and an alignment notch 236. The array of wells includes an exemplary well 120ba, an upper portion 122bb of the well in the second row and second column of the array, a lower portion 124bc of the well in the second row and third column of the array, and an exemplary post 126ad exposed in the well in the first row and fourth column of the array. Not shown in FIG. 4 is a clear cover on the support lip 232'. In one embodiment, the cover has an array or pattern of holes therein corresponding to the locations of the wells 120. In such a case, the cover may function as a mask for application of an adhesive into the wells 120 (e.g., by spraying). The holes in the cover are centered over the wells 120 and have a diameter less than that of the wells 120. The diameter of the holes in the cover may be as small as ¼ to ½ of the size or diameter of the sample beads to be analyzed.

An Exemplary Apparatus for Spectroscopic Analysis and/or Imaging of Coated Beads, Particles or Microparticles In another aspect, the present invention concerns an apparatus for spectroscopic analysis and/or imaging of coated beads, particles or microparticles that includes the present holder; a terahertz radiation source, configured to irradiate beads, particles or microparticles in the holder with pulsed terahertz radiation; and a terahertz radiation detector, configured to receive the pulsed terahertz radiation reflected from the beads, particles or microparticles in the holder. The present terahertz spectroscopy or imaging apparatus may comprise a time-of-flight terahertz spectroscopy and/or imaging system. The coated bead, particle or microparticle may include a coated and/or time-release pharmaceutical formulation in bead or pellet form, comprising an active or inert core, an active or inert layer thereon, and a coating layer on the active or inert layer. In some examples, the core may be a pharmaceutically-acceptable sugar or other excipient, or an active pharmaceutical agent in a pharmaceutically-acceptable carrier, compressed or otherwise formed into a bead, pellet or microparticle. The active or inert layer may be a drug layer coated onto the core, or a pharmaceutical carrier that protects a drug in the core against the acidic environment of a patient's stomach. The coating layer may be a pharmaceutically-acceptable coating for protecting the underlying formulation against the effects of humidity and/or oxygen, or a coating intended to mask the unpleasant flavor of the underlying formulation.

Figure 5:
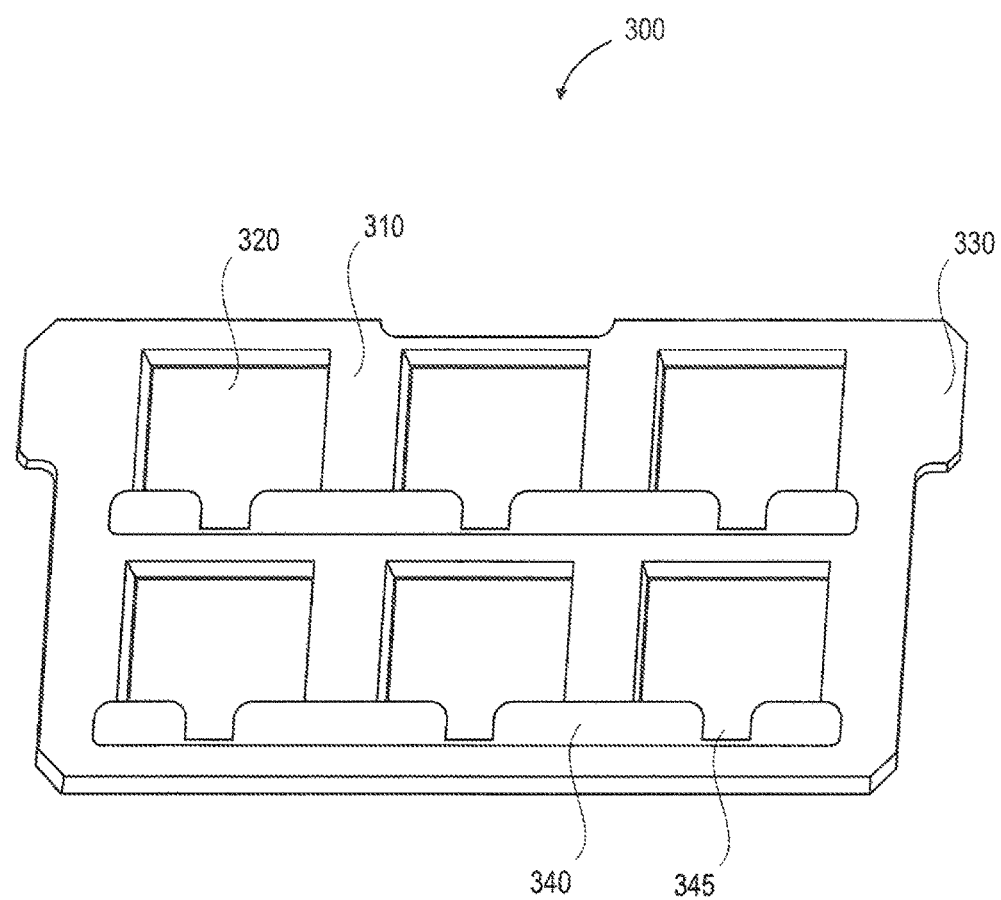
FIG. 5 is a photograph of an exemplary cassette for securely holding multi-well bead holders according to the present invention.

FIG. 5 shows an exemplary cassette 300 containing a number of slots or wells 320 into which the present bead holder can be placed. The slots or wells 320 generally have dimensions configured to hold the bead holder securely in place, although the bead holders can also be held in place using one or more clips, spring-loaded locking mechanisms, covers, etc. Furthermore, although the exemplary cassette 300 includes a 3×2 array of slots 320, any integer number of slots of at least one and/or any arrangement of slots (e.g., in a regularly-spaced x-by-y array, in a radial or circular arrangement, etc.) are possible. The exemplary cassette 300 further includes bars or projections 340 that may lie partially over an edge of the slot 320, with an opening 345 over each slot 320 to facilitate insertion and removal of the bead holder in the slot 320. The cassette 300 further includes a pair of tabs 330 on opposed sides of the cassette 300. The tabs 330 facilitate insertion and removal of the cassette 300 in the terahertz spectroscopy or imaging apparatus, and in some embodiments, may facilitate manipulation of the cassette 300 within the terahertz spectroscopy or imaging apparatus.

Similar to the exemplary bead holder, the cassette 300 may comprise or consist essentially of a relatively rigid and/or high modulus thermoplastic or thermoset polymer. However, the cassette 300 is generally made by a single-step injection molding or other molding process.

Figure 6:
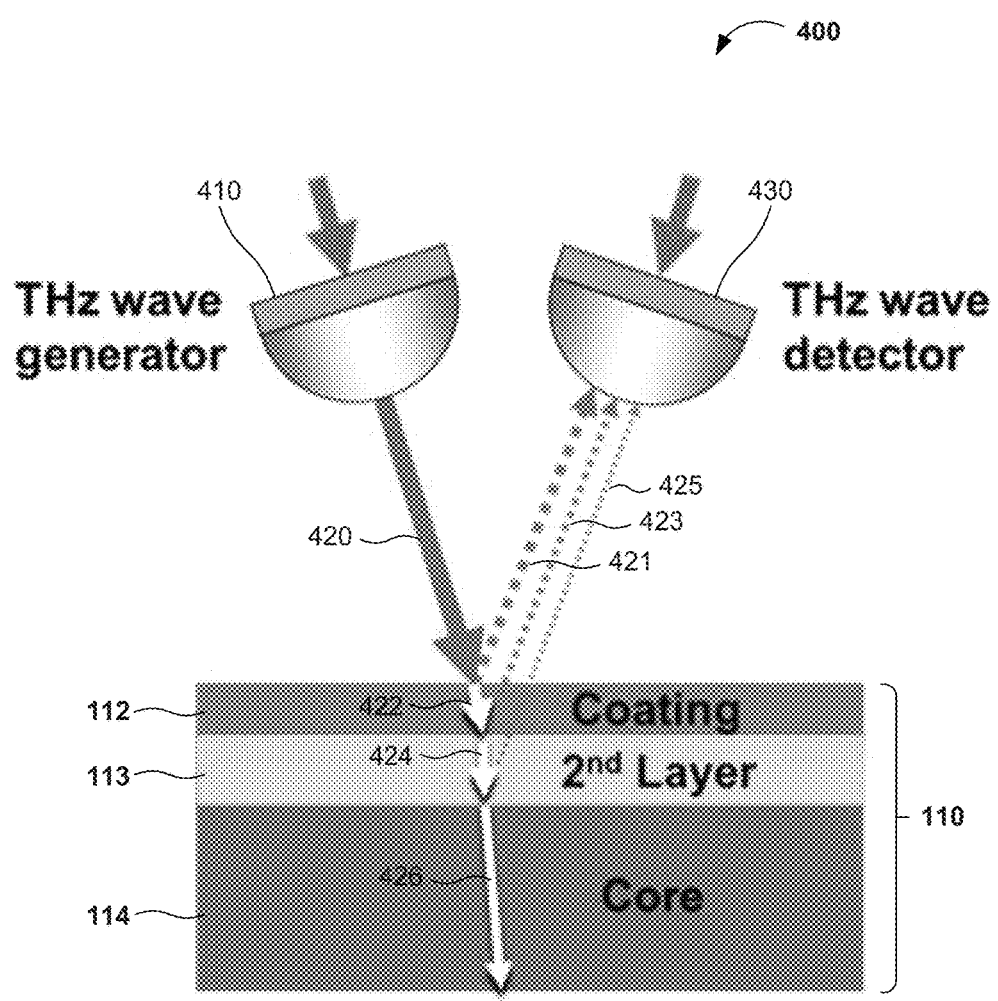
FIG. 6 is a diagram showing an exemplary approach for terahertz spectroscopy and/or imaging of multiple layers of material on a substrate according to the present invention.

FIG. 6 shows an exemplary terahertz spectroscopy and/or imaging apparatus 400. The exemplary terahertz spectroscopy and/or imaging apparatus 400 comprises a terahertz wave generator 410 and a terahertz wave detector 430. The terahertz wave generator 410 is positioned to irradiate the sample 110 with pulses of radiation 420 in the terahertz frequency range (e.g., from 0.3 THz to about 100 THz), and the terahertz wave detector 430 is positioned to receive and detect terahertz-frequency radiation (e.g., waves 421, 423 and 425) reflected by the sample 110. As shown in FIG. 6, sample 110 comprises a core 114, a second layer of material 113 on the core 114, and a coating 112 on the second layer of material 113. An exemplary terahertz radiation pulse 420 impinges on the outer surface of the coating 112. A reflected portion 421 of the pulse 420 is directed towards the terahertz wave detector 430, at roughly the same speed as pulse 420. The reflected portion 421 of the pulse 420 is detected by the terahertz wave detector 430 at a time $t_0$.

The remainder 422 of the pulse 420 enters the coating layer 112, where it slows somewhat (e.g., due to the different refractive index of the coating 112). A portion 423 of the wave 422 is reflected by the outer surface of the second layer 113 towards the terahertz wave detector 430, at roughly the same speed as the wave 422. The reflected portion 423 of the pulse portion 422 is detected by the terahertz wave detector 430 at a time $t_1$. The difference between the times $t_1$ and $t_0$ is directly related to the thickness of the coating 112 (e.g., the greater the time difference, the thicker the coating 112).

The remainder 424 of the wave 422 enters the second layer 113, where it may slow even further (e.g., due to a change in the refractive index of the second layer 113, relative to the coating 112). A portion 425 of the wave 424 is reflected by the outer surface of the core 114 towards the terahertz wave detector 430, at roughly the same speed as the wave 424. The reflected portion 425 of the pulse portion 424 is detected by the terahertz wave detector 430 at a time $t_2$. The difference between the times $t_2$ and $t_1$ is directly related to the thickness of the second layer 113 (e.g., the smaller the time difference, the thinner the second layer 113). An unreflected portion 426 of the pulse 420 passes through the core 114, and is not detected by the terahertz wave detector 430. A terahertz spectroscopy and/or imaging apparatus that determines characteristics of the surface layer(s) of the sample 110 using the difference in detection times (or delay) of radiation waves reflected by the sample 110 is generally known as a "time-of-flight" spectroscopy and/or imaging apparatus.

In one embodiment, the terahertz spectroscopy or imaging apparatus 400 comprises a horizontally-oriented generator 410 and detector 430, in which the radiation pulse 420 is emitted along a path substantially parallel to the floor, ground, table top, and/or other substantially flat, horizontal surface on which the apparatus 400 may be directly or indirectly placed. In such a horizontal apparatus 400, the view in FIG. 6 is from the top down or the bottom up, and the sample 110 is held or positioned so that the surface(s) of the sample and/or surface layers thereof are substantially orthogonal to a point between the generator 410 and the detector 430. The sample 110 may be moved to collect additional data and/or information relating to other locations on the sample 110, and a map, picture (image) or other depiction (e.g., a spectrogram) of the surface and/or surface layers of the sample may be generated. Alternatively, the generator 410 and detector 430 may be moved to collect different reflections from the sample 110.

In other embodiments, the present terahertz spectroscopy or imaging apparatus 400 may comprise a vertically-oriented generator 410 and detector 430, in which the radiation pulse 420 is emitted along a path substantially perpendicular to the floor, ground, table top, and/or other substantially flat, horizontal surface on which the apparatus 400 may be directly or indirectly placed. In such a vertical apparatus 400, the view in FIG. 6 is from the side, and the sample 110 is held or positioned on an x-y table or stage (e.g., a high-speed, high-resolution, motorized x-y table or stage) so that the surface(s) of the sample and/or surface layers thereof are substantially orthogonal to a point between the generator 410 and the detector 430. In the vertical apparatus, the sample 110 is generally moved to collect additional data and/or information relating to other locations on the sample 110 to generate the map, picture (image) or other depiction (e.g., a spectrogram) of the surface and/or surface layers of the sample.

Figure 7A:
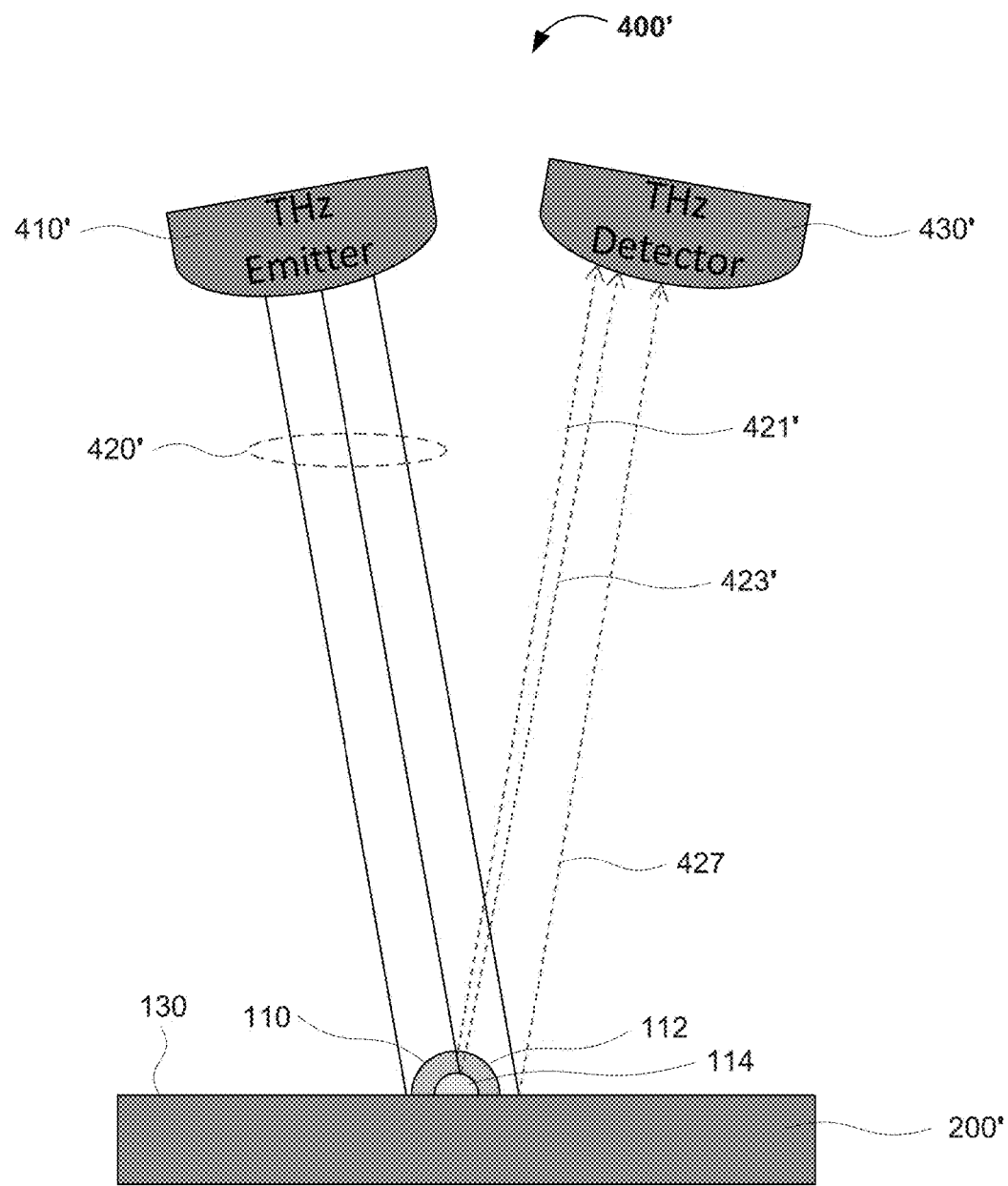
FIGS. 7A-B are diagrams showing exemplary approaches for terahertz spectroscopy and/or imaging of a coated bead according to the present invention.

FIG. 7A shows a more detailed embodiment of the present terahertz spectroscopy or imaging apparatus 400', including an exemplary bead holder 200', holding a bead 110 therein. The terahertz spectroscopy or imaging apparatus 400' also includes a terahertz radiation emitter 410' and a terahertz detector 430', which may be the same as or different from the terahertz wave generator 410 and terahertz wave detector 430 in FIG. 6. The exemplary bead 110 includes a coating 112 and a core 114. Reflected waves 421' and 423' of the pulse 420' from the terahertz radiation emitter 410' are substantially the same as reflected waves 421 and 423 in FIG. 6. However, reflected wave 427 does not pass through any part of the bead 110, but is instead reflected from the substantially horizontal/planar upper surface of the tray 130 of the holder 200' (that has been raised relative to the upper surface of the substrate 50 in FIG. 1). As a result, its delay relative to the detection time $t_0$ of reflected wave 421' is shorter than in the conventional case shown in FIG. 1, and any interference that might be caused by the reflected wave 427 with the reflected wave 423' is avoided by the present holder 200'.

Figure 7B:
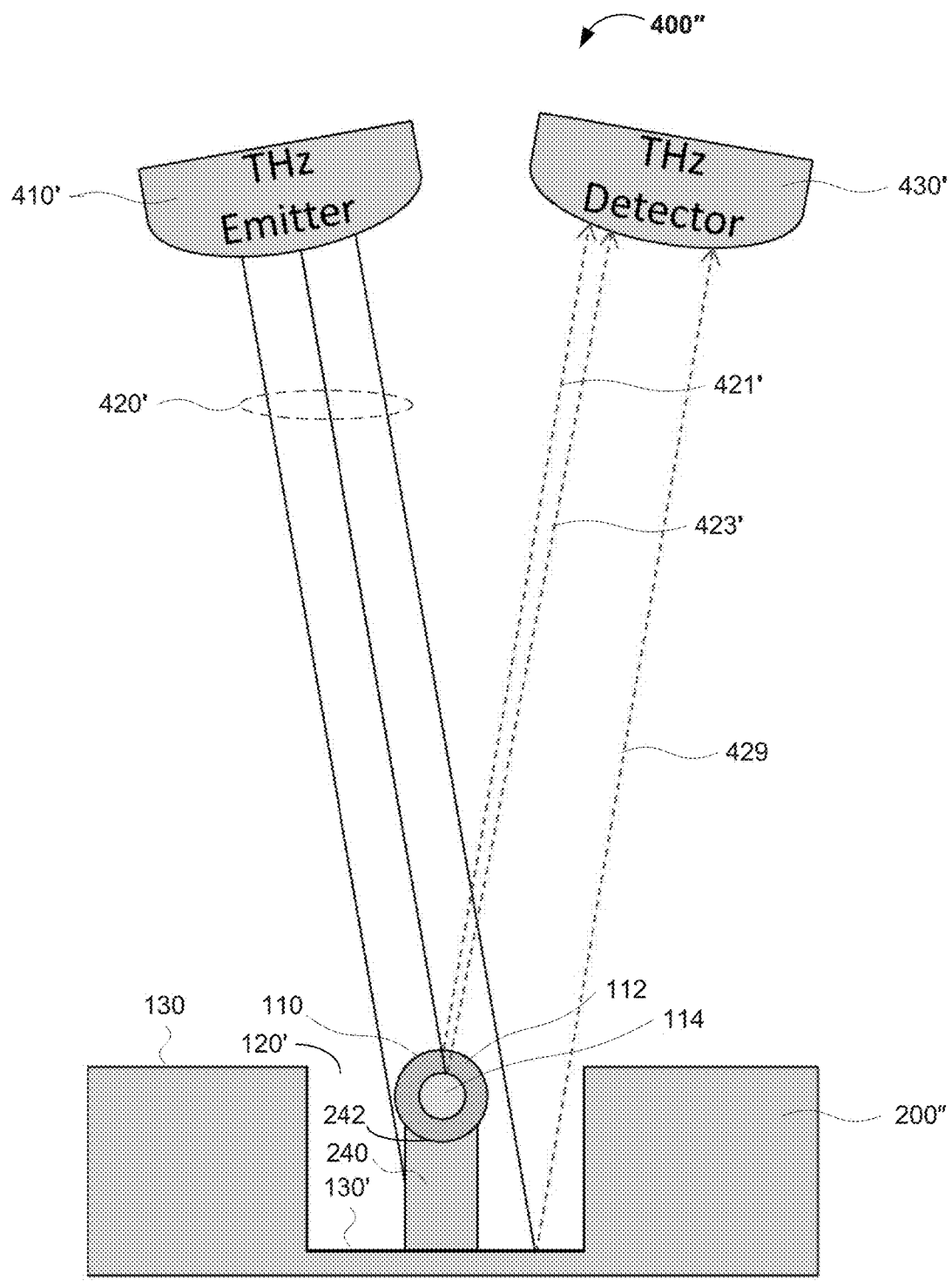

FIG. 7B shows an alternative embodiment of the present terahertz spectroscopy or imaging apparatus 400, including an exemplary bead holder 200, having a well or depression 120 with a post, projection or pillar 240 therein. The post, projection or pillar 240 holds a bead 110 thereon. The terahertz radiation emitter 410' and terahertz detector 430' of terahertz spectroscopy or imaging apparatus 400 may be the same as or different from the terahertz wave generators 410 and 410' and the terahertz wave detectors 430 and 430' in FIGS. 6 and 7A, respectively. The exemplary bead 110 is substantially the same as the bead 110 in FIG. 7A. Reflected waves 421' and 423' of the pulse 420' from the terahertz radiation emitter 410' are also substantially the same as reflected waves 421 and 421', and 423 and 423', in FIGS. 6 and 7A, respectively. However, reflected wave 429, which does not pass through any part of the bead 110, is instead reflected from the substantially horizontal/planar upper surface 242 of the tray 130' of the holder 200 (that has been lowered relative to the upper surface of the substrate 50 in FIG. 1 due to the placement of the bead 110 on the post, projection or pillar 240 having a curved or concave upper surface 242 supporting the bead 110). As a result, the delay of reflected wave 429 relative to the detection time $t_0$ of reflected wave 421' is longer than in the conventional case shown in FIG. 1, and any interference that might be caused by the reflected wave 429 with the reflected wave 423' is avoided by the present holder 200.

In the exemplary bead holder 200" of FIG. 7B, the well or depression 120' may have area dimensions (e.g., length and width, diameter, etc.) greater than the beam width (e.g., the half-power or full-width, half-max beam width) of the terahertz radiation 420' to minimize or eliminate reflections from the uppermost planar surface 130 of the holder 200" outside of the well or depression 120'. However, in the case where reflections of the terahertz radiation 420' from the uppermost planar surface 130 (outside of the well or depression 120') occur, the uppermost surface 242 of the post, projection or pillar 240 may be offset from the uppermost planar surface 130 of the holder 200" by a height or depth sufficient to minimize or eliminate interference between terahertz radiation reflected from the substantially horizontal/planar upper surface 130 and reflections 421' and 423' from the bead on the post, projection or pillar 240.

Figure 8A:
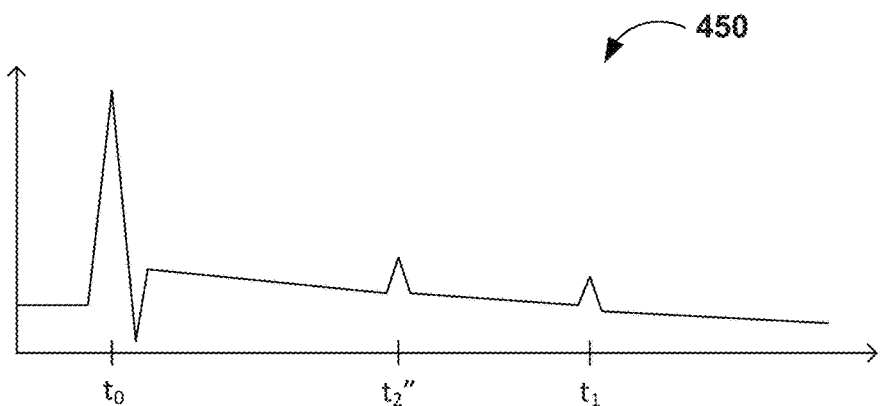
FIGS. 8A-C are graphs representative of comparative results for terahertz spectroscopy and/or imaging of a coated bead in accordance with the present invention and in comparison with the conventional approach shown in FIG. 1.
Figure 8B:
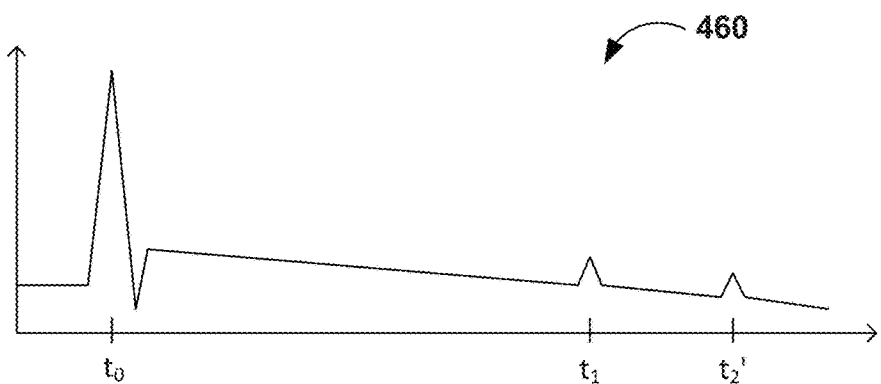
Figure 8C:
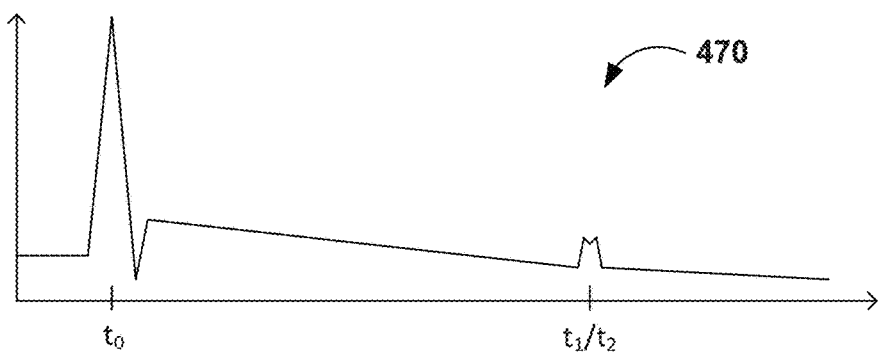

Shown graphically in FIGS. 8A-C, the representative spectrogram 450 in FIG. 8A for the reflections detected by the terahertz detector 430' in the exemplary system of FIG. 7A shows the detection time $t_0$ of reflected wave 421', the detection time $t_1$ of reflected wave 423' from the outer surface of the core 114, and the detection time $t_2$ of reflected wave 427 from the substantially planar upper surface of the tray 130. The peaks for detection of the reflected waves 423' and 427 at times $t_1$ and $t_2$ are clearly separated. Similarly, in FIG. 8B, the representative spectrogram 460 for the reflections detected by the terahertz detector 430' in the exemplary terahertz spectroscopy or imaging apparatus 400 of FIG. 7B shows the detection time $t_0$ of reflected wave 421', the detection time $t_1$ of reflected wave 423' from the outer surface of the core 114, and the detection time $t_2'$. The representative spectrogram 460 of FIG. 8B is also at least qualitatively correct for the reflections detected by the terahertz detector 430 in the exemplary terahertz spectroscopy or imaging apparatus 400 of FIG. 6 (i.e., the detection times $t_0$ of reflected wave 421, $t_1$ of reflected wave 423 from the outer surface of the second layer 113, and $t_2$ of reflected wave 425 from the outer surface of the core 114 are in the same sequence along the x-axis). The peaks for detection of the reflected waves 423 and 429 at times $t_1$ and $t_2$ are also clearly separated.

However, as is shown in the representative spectrogram 470 in FIG. 8C, the reflections detected by the terahertz detector 30 in the exemplary terahertz spectroscopy or imaging apparatus 10 of FIG. 1 shows the same detection time $t_0$ of reflected wave 22, substantially the same detection time $t_1$ of reflected wave 24 from the outer surface of the core 44, and a similar detection time $t_2$ of reflected wave 26 from the upper surface of the bead-mounting substrate 50. The peaks for detection of the reflected waves 24 and 26 at times $t_1$ and $t_2$ are not separated, so it is difficult, if not impossible, to determine which peak or side peak is due to reflected wave 24 and which peak or side peak is due to reflected wave 26. Thus, the present invention solves a need in the fields of terahertz spectroscopy and/or imaging, as well as imaging and/or spectroscopic analysis of coated beads, particles or microparticles.

An Exemplary Method of Spectroscopic Analysis and/or Imaging of Coated Beads, Particles or Microparticles A further aspect of the invention relates to a method of analyzing and/or imaging coated beads, particles or microparticles using terahertz spectroscopy. Typically, the terahertz spectroscopy involves time-of-flight analysis of pulsed beams of terahertz radiation, but the invention is not limited in this manner.

The method of analyzing and/or imaging coated beads, particles or microparticles using the bead holder may comprise the following steps, which may be performed in the following sequence:

Select a bead holder having a well size appropriate for the samples

Remove the sealing device (if any) if the bead holder has an adhesive thereon (e.g., in the wells)

Load beads onto the bead holder

Optionally load the loaded bead holder into or onto a bead holder cassette

Load the bead holder cassette into the imaging/spectroscopy system

Irradiate samples (beads) with pulses of terahertz radiation

Collect reference and sample information from beads and references in bead holder Evaluate data FIG. 9 shows a flow chart for an exemplary method 500 of terahertz spectroscopy and/or imaging of one or more beads in accordance with the present invention. At 510, a bead holder having a well size appropriate for the samples is selected. As described above, when the beads have an average size or diameter of from 0.3 to 1 mm, the depth of the wells in the bead holder may be from 0.1 to 0.6 mm. When the beads have an average size or diameter of from 1 to 3 mm, the depth of the wells may be from 0.6 to 1.0 mm. When the beads have an average size or diameter of from 3 to 5 mm, the depth of the wells may be from 1.0 to 2.0 mm. Furthermore, the wells may have a width of from 1.5 to 5 times the depth of the wells (e.g., 2-3 times, or any value or other range of values therein).

At 520, if the bead holder has an adhesive thereon (e.g., in the wells) that was applied through a pattern of holes in a mask, cover or sealing device, the sealing device is then removed. In such embodiments, the adhesive is generally not on the planar surface of the tray of the bead holder.

At 530, the beads are loaded onto the bead holder. Optionally, reference beads are loaded into one or more predetermined locations in the bead holder. For example, a reference bead may be placed in the well in the first row and first column of the array of wells in the bead holder. Sample beads are loaded into the remaining wells. Although the reference bead may be preloaded or loaded using a narrow-gauge vacuum pipette or tweezers, when the adhesive is only in the wells, the sample beads may be loaded simply by placing the bead holder face down in a larger tray, box or dish of sample beads, removing the bead holder, and gently shaking or brushing sample beads attached to the bead holder by electrostatic force off of the bead holder. The wells generally have dimensions allowing one and only one bead to fit therein, and since the adhesive is only in the well, beads can easily, quickly and efficiently be loaded into the bead holder in this manner. Optionally, the bead holder having sample beads and reference beads loaded therein are loaded into or onto a bead holder cassette (see, e.g., FIG. 5).

Referring back to FIG. 9, at 540, the loaded bead holder or cassette is loaded into a terahertz spectroscopy/imaging system. When the loaded bead holder or cassette is in a predetermined position for data collection (e.g., spectroscopy and/or imaging), the beads (both samples and reference beads) are irradiated with pulses of terahertz radiation at 550. When using a terahertz spectroscopy/imaging apparatus with a stationary pulse/wave generator and detector, the bead holder may be rotated to present a series of surface locations on the beads that are orthogonal to the radiation emitted from the terahertz pulse/wave generator. Thus, an adhesive is generally necessary in the well(s) of a bead holder for such terahertz spectroscopy/imaging apparatuses. However, when using a terahertz spectroscopy/imaging apparatus in which the pulse/wave generator and detector can move, the bead holder is generally not rotated, and an adhesive is generally not necessary in the well(s) of a bead holder for such terahertz spectroscopy/imaging apparatuses.

In general, the pulses are relatively short. For example, in state-of-the-art time-of flight terahertz imaging and/or spectroscopy, the pulse length is on the order of picoseconds, such as from 1 to 10 ps, but other pulse lengths, and even continuous irradiation with one or more terahertz waves, are contemplated by the present invention.

In some embodiments, the pulse(s) and/or detection thereof are divided into a plurality of components in the time domain and/or frequency domain. In one example, pulses of 2-5 ps are divided into $2^{k}*100$ time-based components, where k is an integer of 1 or more (e.g., 4, 6, 8 etc.). When different reflections are detected in different components of the pulse, the different reflections can be distinguished from each other, and information about the thickness of the coating can be determined. For example, a greater number of components in the pulse(s) or detection thereof can lead to greater accuracy and/or more detailed information, and greater confidence in the resulting image and/or spectrogram.

At 560, reflection information/data is collected from reference bead(s) and sample beads in the bead holder. For example, information/data relating to the delay in detection of waves reflected from different surfaces in both the reference bead(s) and the sample beads are collected. Reflection data from the horizontal/planar surface of the bead holder may also be collected, but the advantage of the present invention is that such a reflection is detected in a region of the spectrogram and/or time domain that does not interfere with reflections from the sample beads.

At 570, the data are evaluated. For example, data from the reference bead(s) provide data for calibrating the terahertz spectroscopy/imaging system and/or a baseline for comparison with the data from the sample beads (e.g., for determining the peak or band corresponding to the outer surface of the sample beads and/or an intensity thereof). The raw time-of-flight reflection detection data (e.g., across a two-dimensional map of the sample bead) can be converted into a graph showing the intensity of detected terahertz wave(s) as a function of the depth into the bead (using, for example, an equation known in the art for converting the delay between reflections to the distance between interfaces in a layered or coated sample). Such data and information can also be converted into an image of the bead that conveys three-dimensional information about the bead.

An Exemplary Method of Making a Holder for Spectroscopy and/or Imaging of Coated Beads, Particles or Microparticles The present invention further relates to a method of making a holder for analyzing or imaging beads, particles or microparticles, comprising forming a tray having a substantially planar upper surface, and forming one or more offsets above or below the substantially planar upper surface. Each offset is configured to hold one of the beads, particles or microparticles, and has a height above or a depth below the substantially planar upper surface configured to minimize or eliminate interference between reflections of the terahertz radiation from the tray and reflections of the terahertz radiation from the bead, particle or microparticle in or on the offset.

The tray and/or the offset(s) may be formed by a single injection-molding operation or by three-dimensional printing, using techniques known in the art. However, the tray and a support structure therefor can also be made by the following two-part process. The first part of the following two-part process can also be used to make a one-part bead holder in which the offset(s) comprise a projection or post above the substantially horizontal/planar upper surface of the tray.

Figure 10:
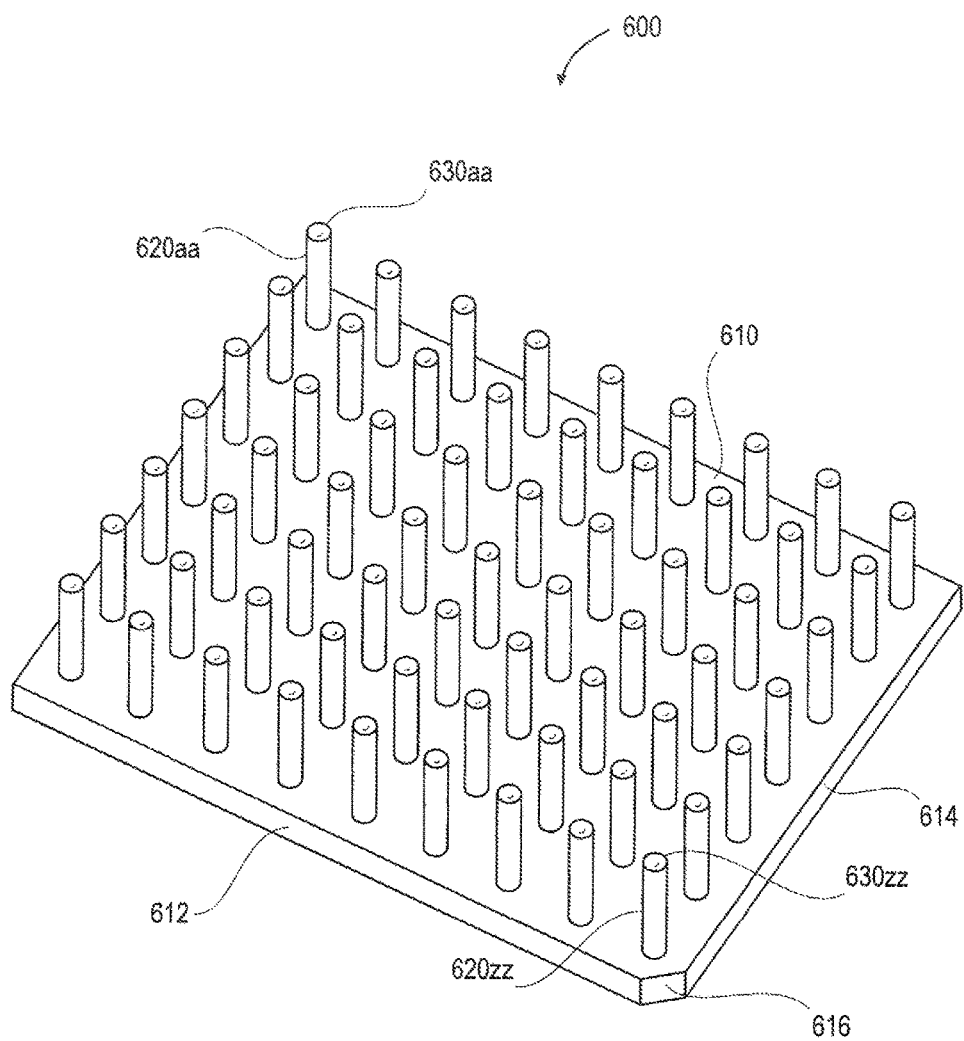
FIG. 10 is a diagram showing an exemplary bead holder including multiple offsets (e.g., posts or projections) according to an embodiment of the present invention, or alternatively, an exemplary bottom section of an exemplary multi-well bead holder in accordance with the present invention.

FIG. 10 shows an exemplary support structure 600 comprising a substantially horizontal/planar base 610 and a plurality of projections or posts 620*aa*-620*zz* thereon. The support structure can be manufactured by molding (e.g., compression molding, injection molding, transfer molding, etc.), generally in a single step. The projections or posts 620*aa*-620*zz* may have a curved and/or concave uppermost surface 630*aa*-630*zz*. In some embodiments, the uppermost surface 630*aa*-630*zz* of the projections or posts 620*aa*-620*zz* have an adhesive thereon. The adhesive may be applied by dipping the uppermost portion of the projections or posts 620*aa*-620*zz* into an adhesive or adhesive-containing solution, or by rolling an adhesive-coated roller across the uppermost surfaces 630*aa*-630*zz* of the projections or posts 620*aa*-620*zz*, etc.

In one embodiment, the support structure 600 with adhesive-tipped projections or posts 620*aa*-620*zz* can function as a bead holder according to the present invention. The uppermost surfaces 630*aa*-630*zz* of the projections or posts 620*aa*-620*zz* are offset from the uppermost surface of the substantially horizontal/planar base 610. Each projection or post 620*aa*-620*zz* is configured to hold one bead, and each projection or post 620*aa*-620*zz* has a height configured to minimize or eliminate interference between terahertz radiation reflected from the substantially horizontal/planar upper surface of the base 610 and reflections of the terahertz radiation from the beads on the projections or posts 620aa-620zz. However, in such an embodiment, the height of the projections or posts 620aa-620zz can be at least the average size or diameter of the sample beads (e.g., at least 2, 3, 5 or more times the average size or diameter of the sample beads).

Figure 11:
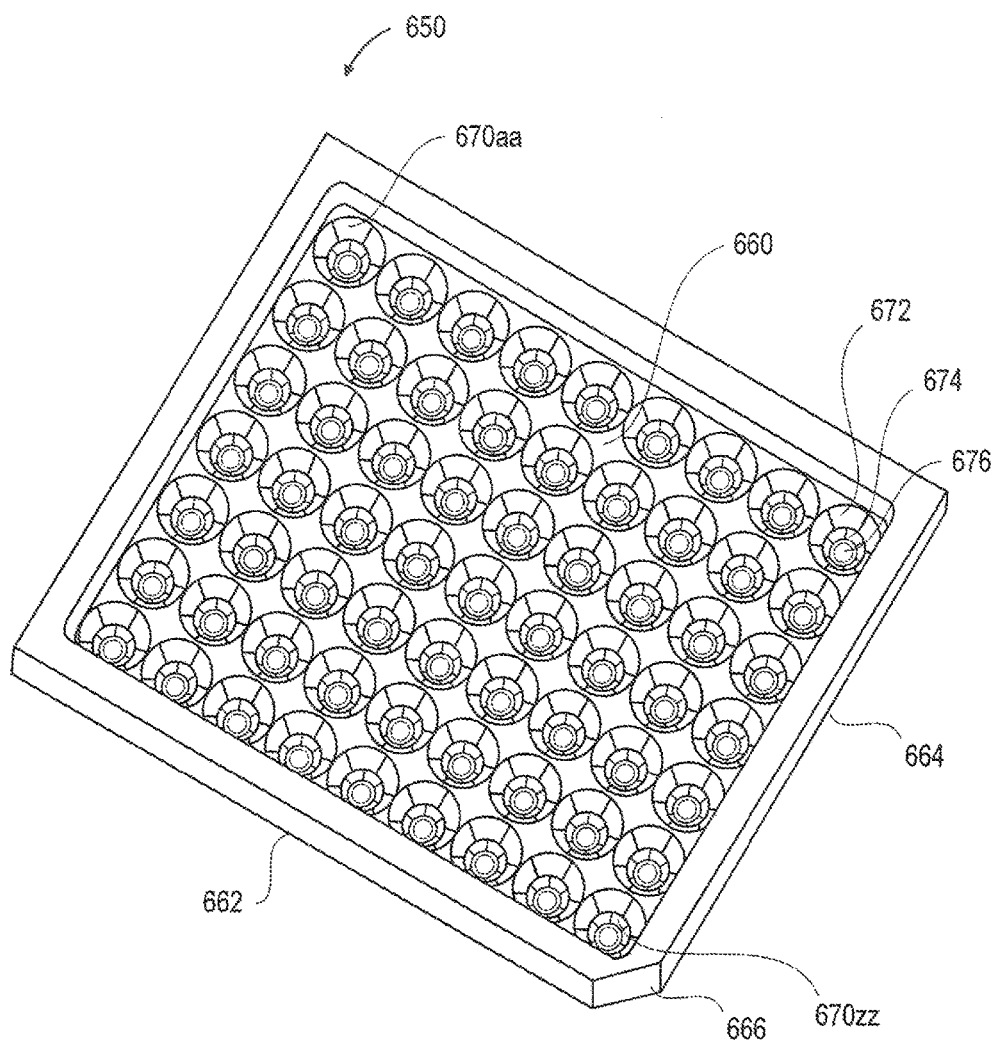
FIG. 11 is a diagram showing an exemplary top section of an exemplary multi-well bead holder in accordance with the present invention, configured to mate with the exemplary bottom section shown in FIG. 10.

FIG. 11 shows an exemplary tray 650 having a substantially horizontal/planar upper surface 660 and an array of wells 670aa-670zz therein, similar to the bead holder shown in FIG. 3. Each of the wells 670aa-670zz includes an upper portion 672, a lower portion 674, and an opening 676 at the bottom of the lower portion 674. The upper portion 672 is wider than the lower portion 674, and has a planar, angled, conical upper surface or a curve, partial toroidal upper surface. The lower portion 674 is substantially cylindrical, in the example of FIG. 11. The exemplary tray 650 can be manufactured by molding (e.g., compression molding, injection molding, thermoforming, extrusion molding, etc.), generally in a single step.

The opening 676 has a shape and/or dimension(s) configured to mate with the uppermost portion of the projections or posts 620aa-620zz of the support structure 600 in FIG. 10. When the sidewalls 662 and 664 and the alignment notch 666 of the tray 650 (FIG. 11) have a height substantially corresponding to the combined depth of the wells 670aa-670zz, height of the projections or posts 620aa-620zz of the support structure 600 (FIG. 10), and thickness of the base 610, and the tray 650 has peripheral dimensions corresponding to (or slightly larger than) the base 610 of the support structure 600, the tray 650 can simply snap onto the support structure 600, thereby facilitating a simple, cost-efficient method of manufacturing the present bead holder. In embodiments where the adhesive is not applied to the support structure 600 prior to assembly with the tray 650, a mask having a pattern of holes corresponding to the wells 670aa-670zz can be placed over the tray 650 as described herein, and adhesive (e.g., a solution containing the adhesive and one or more volatile solvents) can be sprayed into the wells 670aa-670zz. However, in the case of terahertz imaging/spectroscopy systems in which the bead holder is held in place on an x-y table or stage, an adhesive is not necessary. Nonetheless, the adhesive may be advantageous for loading and holding the beads securely in the holder.

CONCLUSION/SUMMARY

Thus, the present invention provides a holder for beads, particles or microparticles, an apparatus for terahertz spectroscopy or imaging of such beads, particles or microparticles, and methods of terahertz spectroscopic analysis or imaging of such beads, particles or microparticles and of making such a holder. The holder generally comprises a tray having a substantially planar upper surface, and one or more offsets above or below the substantially planar upper surface. Each offset is configured to hold one of the beads, particles or microparticles, and has a height or depth configured to minimize or eliminate interference between reflections of the terahertz radiation from the tray and reflections of the terahertz radiation from the bead, particle or microparticle in or on the offset. The terahertz spectroscopy/imaging apparatus generally includes the present holder, and the method of terahertz spectroscopic analysis or imaging of beads, particles or microparticles generally employs the present holder.

The invention advantageously eliminates radiation reflected by the holder or support substrate in the measured signal from the sample, which contaminates the data analysis. Thus, the present invention advantageously provides a holder, apparatus and method for terahertz imaging and/or spectroscopy that reduce or eliminate interference from reflections from the holder that might otherwise have a comparable time of flight to reflections from the beads, particles, microparticles or other similar samples. This has particular advantage in the field of pharmaceutical formulations in the form of coated beads or pellets, where rapid and non-destructive analysis of such formulations and the physical forms thereof is highly desired.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A holder for beads, particles or microparticles, comprising:
   a) a tray having a substantially planar upper surface; and
   b) one or more offsets above or below the substantially planar upper surface, each offset being configured to hold one of the beads, particles or microparticles and having a height or depth configured to minimize or eliminate interference between reflections of terahertz radiation from the tray and reflections of terahertz radiation from the bead, particle or microparticle in or on the offset, and wherein the one or more offsets comprise a plurality of depressions and/or wells below the substantially planar upper surface of the tray.

2. The holder of claim 1, wherein the plurality of depressions and/or wells are configured to hold beads, particles or microparticles having an average diameter or size greater than a depth of the plurality of depressions and/or wells.

3. The holder of claim 2, wherein the plurality of depressions and/or wells have a width of from 1.5 to 5 times the depth of the plurality of depressions and/or wells.

4. The holder of claim 2, wherein each of the plurality of depressions and/or wells has a first portion at the substantially planar upper surface of the tray and a second portion below the first portion, the second portion having an outer periphery entirely within an outer periphery of the first portion, the first portion having an uppermost surface at a first angle or arc with respect to the substantially planar upper surface of the tray, and the second portion having an uppermost surface at a second angle or arc with respect to the uppermost surface of the first portion, the second angle or arc being equal to or greater than the first angle or arc.

5. The holder of claim 1, wherein the one or more offsets comprise a plurality of projections or posts above the substantially planar upper surface of the tray.

6. The holder of claim 5, wherein the plurality of projections or posts are configured to hold beads, particles or microparticles having an average diameter or size greater than a width of the plurality of projections or posts.

7. The holder of claim 1, wherein the tray comprises one or more dielectric materials forming the substantially planar upper surface.

8. The holder of claim 1, wherein the one or more offsets comprise an array of offsets having n rows and m columns, n and m each independently being an integer of at least 2.

9. The holder of claim 8, wherein n and m are each independently an integer of at least 4, and at least one offset is reserved for reference beads, particles or microparticles.

10. The holder of claim 1, further comprising an adhesive on an uppermost surface of each of the one or more offsets.

11. The holder of claim 1, wherein the height or depth of each of the one or more offsets from the substantially planar upper surface is from 0.1 to 3 mm.

12. A terahertz spectroscopy or imaging apparatus, comprising:
   a) holder of claim 1;
   b) a terahertz radiation source, configured to irradiate beads, particles or microparticles in the holder with pulsed terahertz radiation; and
   c) a terahertz radiation detector, configured to receive the pulsed terahertz radiation reflected from the beads, particles or microparticles in the holder.

13. The terahertz spectroscopy or imaging apparatus of claim 12, comprising a time-of-flight terahertz spectroscopy and/or imaging system.

14. A method of analyzing or imaging beads, particles or microparticles, comprising:
   a) loading one or more beads, particles or microparticles onto a bead holder, the bead holder comprising a tray having a substantially planar upper surface and one or more offsets above or below the substantially planar upper surface, each offset being configured to hold one of the beads, particles or microparticles and having a height or depth configured to minimize or eliminate interference between reflections of terahertz radiation from the tray and reflections of the terahertz radiation from bead, particle or microparticle in or on the offset, and wherein the one or more offsets comprise a plurality of depressions and/or wells below the substantially planar upper surface of the tray;
   b) loading the bead holder into a terahertz spectroscopy and/or imaging system;
   c) irradiating the one or more beads, particles or microparticles in the bead holder with pulses of terahertz radiation; and
   d) evaluating and/or analyzing data and/or information from reflections of the pulses of terahertz radiation from the one or more beads, particles or microparticles in the bead holder.

15. The method of claim 14, wherein the beads, particles or microparticles comprise coated beads, particles or microparticles.

16. The method of claim 14, wherein the bead holder further comprises (i) an adhesive on an uppermost surface of each offset and (ii) a cover or sealing device on or over the adhesive.

17. The method of claim 16, further comprising removing the cover or sealing device prior to loading the one or more beads, particles or microparticles onto the bead holder.

18. The method of claim 14, wherein each offset is configured to hold one bead, particle or microparticle, the depth of each offset is less than an average diameter or size of the one or more beads, particles or microparticles when the offset is below the substantially planar upper surface of the tray, and each offset has a width less than an average diameter or size of the one or more beads, particles or microparticles when the offset is above the substantially planar upper surface of the tray.

19. The method of claim 14, further comprising loading the loaded bead holder into or onto a cassette, and loading the cassette into the imaging system.

20. The method of claim 4, wherein the one or more offsets comprise an array of offsets having n rows and m columns, n and m each independently being an integer of at least 2, and the method further comprises loading one or more reference beads or particles in the bead holder, and collecting reflection information from the one or more reference beads and the one or more beads, particles or microparticles in the bead holder.

21. The method of claim 14, wherein the terahertz spectroscopy and/or imaging system is a time-of-flight terahertz spectroscopy and/or imaging system.

22. A method of making a holder for analyzing or imaging beads, particles or microparticles, comprising:
   a) forming a tray having a substantially planar upper surface; and
   b) forming one or more offsets above or below the substantially planar upper surface, each offset being configured to hold one of the beads, particles or microparticles and having a height above or a depth below the substantially planar upper surface configured to minimize or eliminate interference between reflections of the terahertz radiation from the tray and reflections of terahertz radiation from the bead, particle or microparticle in or on the offset, and wherein the one or more offsets comprise a plurality of depressions and/or wells below the substantially planar upper surface of the tray.

23. The method of claim 22, wherein the tray and the one or more offsets are formed by a single injection-molding operation or by three-dimensional printing.

24. The method of claim 23, wherein the tray and the one or more offsets are formed by a first single injection-molding operation, and the method further comprises performing a second single injection-molding operation to form a base and one or more posts or projections, each of the one or more posts or projections configured to support a unique one of the one or more offsets, and pressing together the tray and the one or more offsets with the base and the one or more posts or projections to form the bead holder.

* * * * *